United States Patent [19]
Brewer et al.

[11] Patent Number: 5,944,742
[45] Date of Patent: Aug. 31, 1999

[54] AAMI SPECIFICATION OPTIMIZED TRUNCATED EXPONENTIAL WAVEFORM

[75] Inventors: James E. Brewer, Cottage Grove; Kenneth F. Olson, Edina, both of Minn.

[73] Assignee: SurVivaLink Corporation, Minneapolis, Minn.

[21] Appl. No.: 09/057,189

[22] Filed: Apr. 8, 1998

Related U.S. Application Data

[60] Provisional application No. 60/041,866, Apr. 8, 1997.

[51] Int. Cl.⁶ ......................................................... A61N 1/39
[52] U.S. Cl. ..................................................... 607/6; 607/7
[58] Field of Search .................................... 607/5, 6, 7, 8

[56] References Cited

U.S. PATENT DOCUMENTS

| | | |
|---|---|---|
| 4,768,512 | 9/1988 | Imran . |
| 5,088,489 | 2/1992 | Lerman ........................................ 607/7 |
| 5,230,336 | 7/1993 | Fain et al. . |
| 5,391,186 | 2/1995 | Kroll et al. . |
| 5,431,686 | 7/1995 | Kroll et al. . |
| 5,593,427 | 1/1997 | Gilner et al. . |
| 5,601,612 | 2/1997 | Gilner et al. . |
| 5,607,454 | 3/1997 | Cameron et al. . |
| 5,645,571 | 7/1997 | Olson et al. . |
| 5,733,310 | 3/1998 | Lopin et al. ................................ 607/7 |

FOREIGN PATENT DOCUMENTS

| | | |
|---|---|---|
| WO 95/09673 | 4/1995 | WIPO . |
| WO 95/32020 | 11/1995 | WIPO . |

OTHER PUBLICATIONS

On The Intensity–Time Relations for Stimulation by Electric Currents. II, H.A. Blair, The Journal of General Physiology, Rockefeller Institute for Medical Research, vol. 15, pp. 731–755, 1932.

Optimal Truncation of Defibrillation Pulses, Werner Irnich, Pacing and Clinical Electrophysiology, Futura Publishing Co., vol. 18, No. 4, pp. 673–688, Apr. 1995.

(List continued on next page.)

*Primary Examiner*—Scott M. Getzow
*Attorney, Agent, or Firm*—Patterson & Keough, P.A.

[57] ABSTRACT

A method of generating and applying a defibrillation shock of the present invention includes first applying a defibrillation shock pulse to a patient with an initial predetermined amount of energy not based on a patient-dependent electrical parameter, and while monitoring a patient-dependent electrical parameter. Next, patient transthoracic impedance is determined based on the patient-dependent electrical parameter. Finally, a subsequent predetermined amount of energy is applied to the patient based on the patient transthoracic impedance calculated above and while monitoring the patient-dependent electrical parameter. Subsequent defibrillation shock pulses are applied using a patient impedance based on the patient-dependent electrical parameter observed during the most recent defibrillation shock. In this manner, an optimal combination of charged voltage and the maximum allowed current (under the AAMI defibrillation waveform standard) is applied for a patient's given transthoracic impedance.

31 Claims, 8 Drawing Sheets

OTHER PUBLICATIONS

Choosing the Optimal Monophasic and Biphasic Waveforms for Ventricular Defibrillation, G.P. Walcott, R. G. Walker, A. W. Cates, W. Krassowska, W.M. Smith, R.E. Ideker, Journal of Cardiovascular Electrophysiology, Futura Publishing Co., vol. 6, No. 9, pp. 737–750, Sep. 1995.

Optimizing Defibrillation Through Improved Waveforms, Michael Block and Günter Breithardt, Pacing and Clinical Electrophysiology, Futura Publishing Co., vol. 18, No. 3, Part II, pp. 526–538, Mar. 1995.

A Conceptual Basis for Defibrillation Waveforms, Brian G. Cleland, Pacing and Clinical Electrophysiology, Futura Publishing Co., vol. 19, No. 8, pp. 1186–1195, Aug. 1996.

A Minimal Model of the Single Capacitor Biphasic Defibrillation Waveform, Mark W. Kroll, Pacing and Clinical Electrophysiology, Futura Publishing Co., vol. 17, No. 11, Part I, pp. 1782–1792, Nov. 1994.

On The Intensity–Time Relations For Stimulation By Electric Currents, I, H.A. Blair, The Journal of General Physiology, Rockefeller Institute for Medical Research, vol. 15, pp. 709–729, 1932.

Ventricular Defibrillation Using Biphasic Waveforms: The Importance of Phasic Duration, A.S.L. Tang, S. Yabe, J.M. Wharton, M. Doker, W.M.Smith, R.E. Ideker, Journal of the American College of Cardiology, American College of Cardiology, vol. 13, No. 1, pp. 207–214, Jan. 1989.

A Minimal Model of the Monophasic Defibrillation Pulse, Mark W. Kroll, Pacing and Clinical Electrophysiology, Futura Publishing Co., vol. 16, No. 4, Part I, pp. 769–777, Apr. 1993.

Strength–Duration and Probability of Success Curves for Defibrillation With Biphasic Waveforms, S.A. Feeser, A.S.L. Tang, K.M. Kavanagh, D.L. Rollins, W.M. Smith, P.D. Wolf, R.E. Ideker, Circulation, American Heart Association, vol. 82, No. 6, pp. 2128–2141, Dec. 1990.

Improved Defibrillation Thresholds With Large Contoured Epicardial Electrodes and Biphasic Waveforms, E.G. Dixon, A.S.L. Tang, P.D. Wolf, J.T. Meador, M.J. Fine, R.V. Calfee, R.E. Ideker, Circulation, American Heart Association, vol. 76, No. 5, pp. 1176–1184, Nov. 1987.

Truncated Biphasic Pulses for Transthoracic Defibrillation, G.H. Bardy, B.E. Gliner, P.J. Kudenchuk, J.E. Poole, G.L. Dolack, G. K. Jones, J. Anderson, C. Troutman, G. Johnson, Circulation, American Heart Association, vol. 91, No. 6, pp. 1768–1774, Mar. 1995.

Transthoracic Defibrillation of Swine With Monophasic and Biphasic Waveforms, B.E. Gliner, T.E. Lyster, S.M. Dillion, G.H. Bardy, Circulation, American Heart Association, vol. 92, No. 6, pp. 1634–1643, Sep. 1995.

Multicenter Comparison of Truncated Biphasic Shocks and Standard Damped Sine Wave Monophasic Shocks for Transthoracic Ventricular Defibrillation, G.H. Bardy, F.E. Marchlinski, A.D. Sharma, S.J. Worley, R.M. Luceri, R. Yee, B.D. Halperin, C.L. Fellows, T.S. Ahern, D.A. Chilson, D.L. Packer, D.J. Wilber, T.A. Mattioni, R. Reddy, R.A. Kronmal, R. Lazzara, Circulation, American Heart Associate, vol. 94, No.10, pp. 2507–2514, Nov. 1996.

Cardiac Defibrillator Devices, 3rd Edition, AAMI/FDS DF2, Association for the Advancement of Medical Instrumentation, Arllington, Virginia, p. ii–60, 1996.

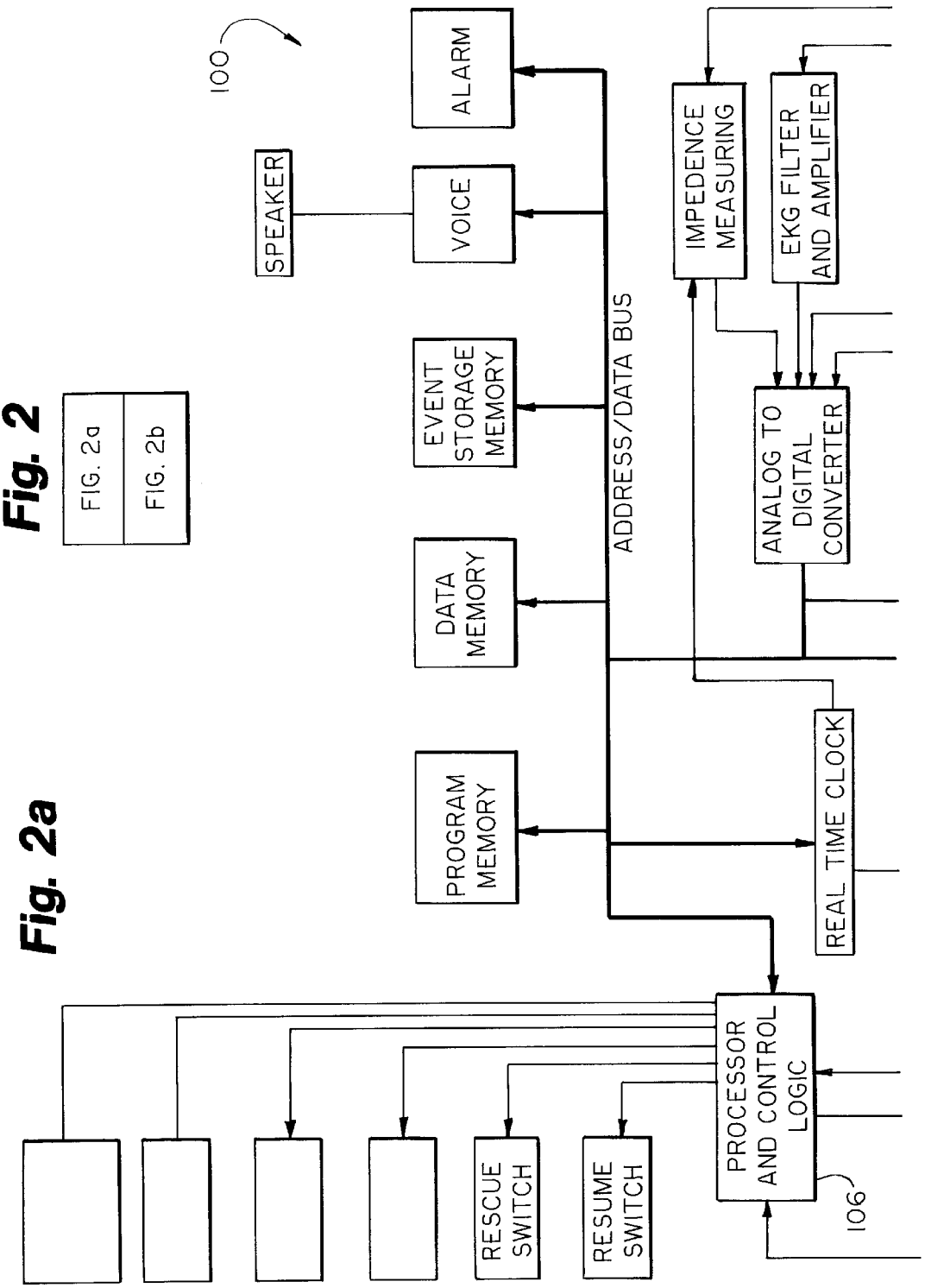

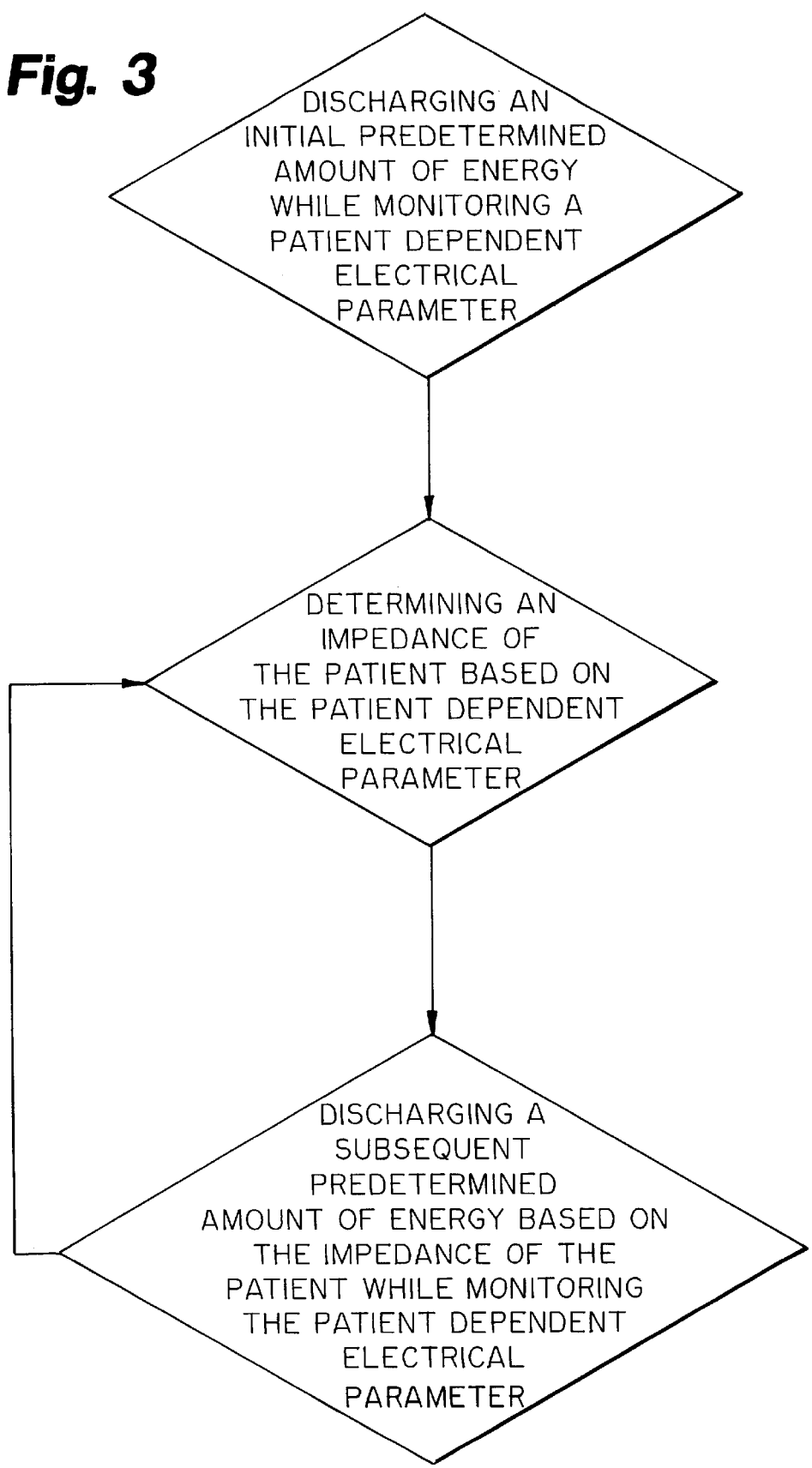

VOLTAGE CURVE

CURRENT CURVE

VOLTAGE CURVE

CURRENT CURVE

VOLTAGE CURVE

CURRENT CURVE 5,944,742

AAMI SPECIFICATION OPTIMIZED TRUNCATED EXPONENTIAL WAVEFORM

CROSS-REFERENCES TO RELATED INVENTIONS

This application is related to U.S. Provisional Application No. 60/041,866, filed Apr. 8, 1997, the content of which is herein incorporated by reference, and priority to which is claimed according to 35 U.S.C. § 119(e).

BACKGROUND OF THE INVENTION

The present invention relates to an automated external defibrillator (AED). More particularly, the present invention relates to an AED that provides an improved defibrillation shock pulse to a patient that is consistent with the most recent Association for the Advancement of Medical Instrumentation (AAMI) specification for cardiac defibrillator devices.

Cardiac arrest, exposure to high voltage power lines and other trauma to the body can result in ventricular fibrillation which is the rapid and uncoordinated contraction of the myocardium. The use of external defibrillators to restore the heart beat to its normal pace through the application of an electrical shock is a well recognized and important tool in resuscitating patients. External defibrillation is used in emergency settings in which the patient is either unconscious or otherwise unable to communicate.

As part of its activities, the AAMI produces a standard for cardiac defibrillator devices. The standard is intended to provide minimum labeling, performance, and safety requirements to establish a reasonable level of safety and efficacy for cardiac defibrillator devices. The AAMI specification governs the parameters of a defibrillation shock pulse delivered by an AED to a patient.

The current applied to a patient during delivery of a defibrillation shock pulse is directly dependent upon the transthoracic impedance of the patient. This characteristic is a simple ohms law relationship. In the past, the AAMI specification assumed that the transthoracic impedance of an average patient was 50 ohms and was designed to cover a range of patient impedance extending from 25 ohms to 100 ohms. However, the impedance of the average patient is actually closer to approximately 80 ohms with some patients having impedances up to 125 or 150 ohms.

Under the past AAMI specification, patients having a higher impedance frequently received substantially less current than patients having a lower impedance. This relationship is exactly the opposite of what is desired. In particular, the AAMI specification mandated that a 25 ohm impedance patient receive 80 maximum peak amperes, a 50 ohm patient receive a 40 maximum peak amperes, and a 100 ohm patient receive 20 maximum peak amperes. Accordingly, with the prior AAMI specification, the current delivered to the patient was inversely proportional to patient transthoracic impedance. Moreover, under the prior AAMI specification, defibrillation shock pulses in the AED were implemented by charging a capacitor bank to 2000 volts and then delivering the energy to the patient with a constant 2000 volts for all levels of patient impedance. The maximum current would exactly match the AAMI specification. The waveform was then truncated after a period of delivery when the appropriate amount of energy had been delivered (e.g. 360 Joules).

The most recent AAMI specification adds a parameter for a 125 ohm patient in which the maximum allowed current for the patient is 20 amperes. In addition, with the most recent AAMI specification, the voltage applied to the patient may be varied depending upon the impedance of the patient. Given these relationships and the greater flexibility allowed by the most recent AAMI standard, an optimal defibrillation shock pulse waveform having the maximum allowable current for each patient is desired for use in AEDs.

SUMMARY OF THE INVENTION

A method of generating and applying a defibrillation shock pulse of the present invention includes first applying a defibrillation shock pulse to the patient with an initial predetermined amount of energy not based on the monitored patient-dependent electrical parameter, and while monitoring a patient-dependent electrical parameter. Next, patient transthoracic impedance is determined based on a patient-dependent electrical parameter. Finally, a subsequent predetermined amount of energy is applied to the patient based on the patient transthoracic impedance calculated above and while monitoring the patient-dependent electrical parameter. Subsequent defibrillation shock pulses are applied using a patient impedance based on the patient-dependent electrical parameter observed during the most recent defibrillation shock. In this manner, an optimal combination of charged voltage and the maximum allowed current (under the AAMI defibrillation waveform standard) is applied for a patient's given transthoracic impedance.

BRIEF DESCRIPTION OF THE DRAWINGS

FIG. 3 is a schematic diagram illustrating a flowchart of a method of generating a defibrillation waveform of the present invention.

DETAILED DESCRIPTION OF THE PREFERRED EMBODIMENTS

Figure 1:
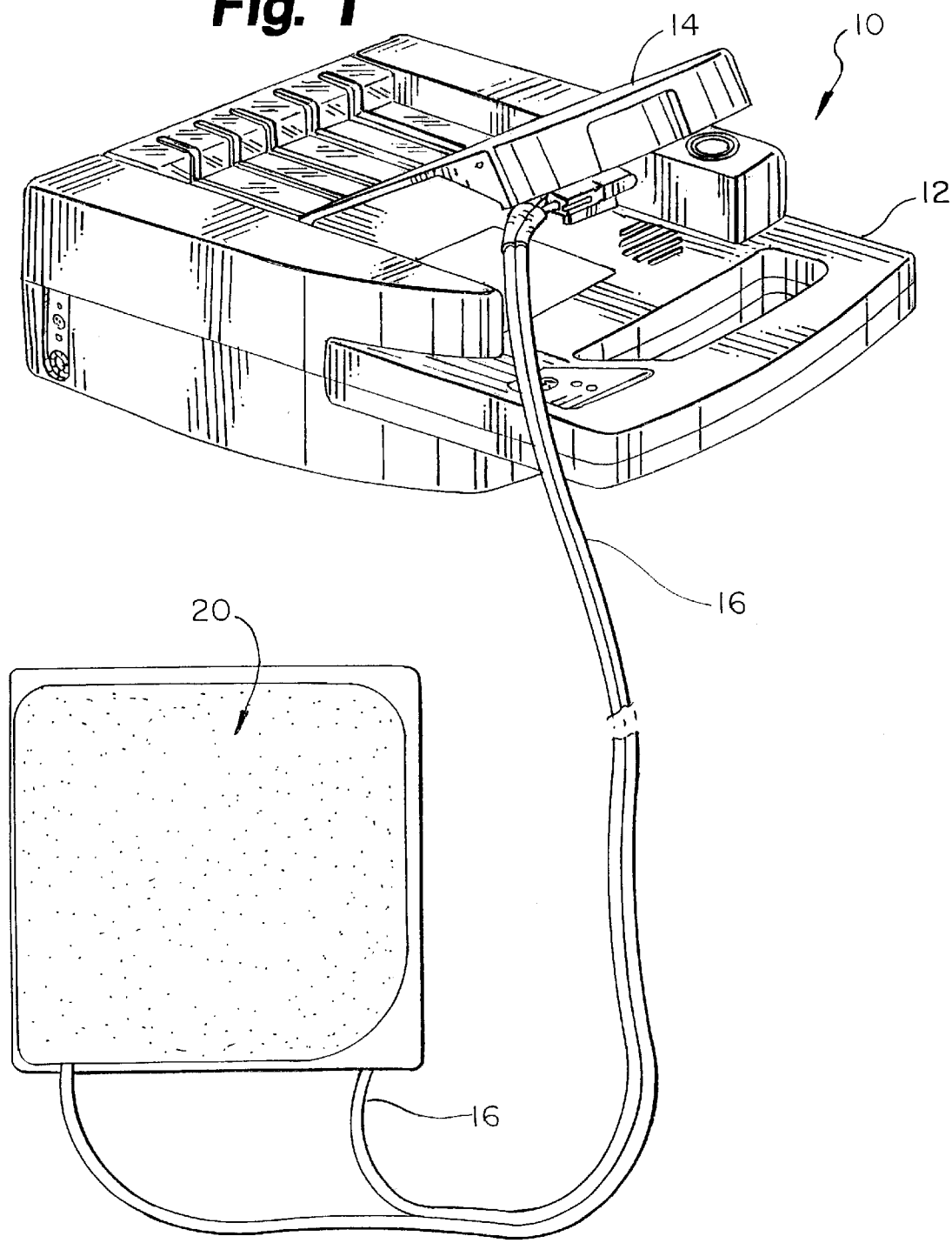
FIG. 1 is a perspective view of an automatic external defibrillator for use with the present invention.

A method of generating defibrillation waveforms of the present invention is preferably adapted for use with an automated external defibrillator (AED). An AED 10 in accordance with the present invention is illustrated generally in FIG. 1. As shown in FIG. 1, defibrillator 10 includes plastic case 12 and a pair of electrodes 20 extendable from openable and closable lid 14 (via lead wires 16) for placement on a patient for delivering a defibrillation shock pulse with AED 10. The shock pulses delivered by AED 10 may be monophasic or biphasic, damped sine waveforms or truncated exponential waveforms, or any other waveforms known to those skilled in the art.

AED 10 is used for emergency treatment of victims of cardiac arrest and is typically used by first responders. AED 10 automatically analyzes a patient's cardiac electrical signal and advises the user to shock a patient upon detection of: (1) ventricular fibrillation; (2) ventricular tachycardia; (3) or other cardiac rhythms with ventricular rates exceeding 180 beats per minute and having amplitudes of at least 0.15 millivolts. When such a condition is detected, AED 10 will build up an electrical charge for delivery to the patient to defibrillate the patient with a defibrillation shock. The operator of AED 10 is guided through the application of a defibrillation shock by voice prompts, an audible charging indicator tone, and an illuminated rescue (shock) initiation button. Olson, et al. U.S. Pat. No. 5,645,571 discloses the general construction and manner of use of an AED, is hereby incorporated by reference, and is commonly assigned to the assignee of the present application.

Figure 2B:
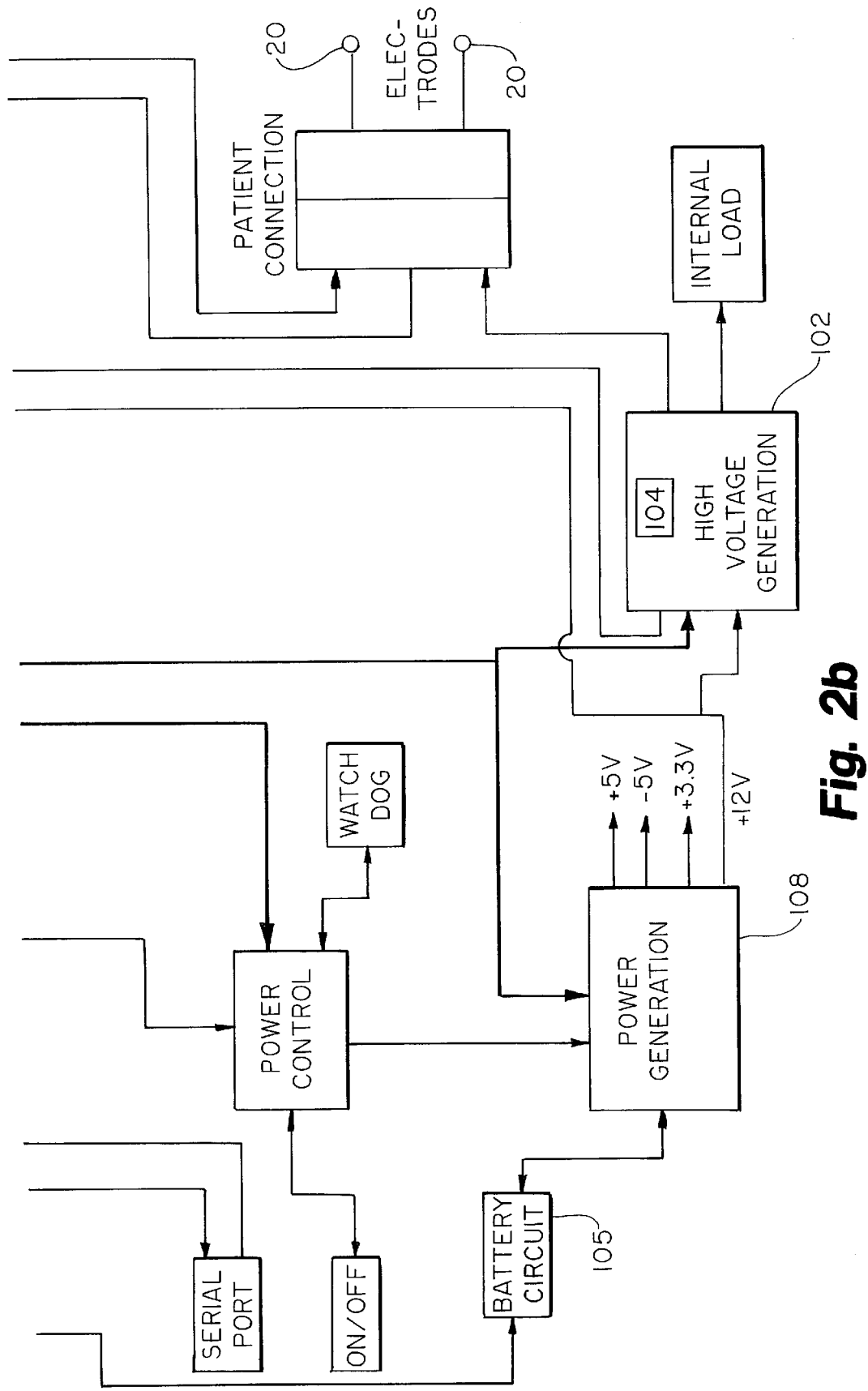
FIG. 2 is a schematic diagram of an electrical control system of a defibrillator for use in a method of generating a defibrillation waveform of the present invention.

As shown in FIG. 2, AED 10 incorporates electrical system 100 including high voltage generation circuit 102 with capacitor bank 104 for charging and delivering a defibrillation shock pulse to the patient, as is known in the art. Microprocessor 106 of AED electrical system 100 controls capacitor bank 104 of circuit 102 and the accompanying electrical system components shown in FIG. 2. Battery circuit 105 powers AED 10 and is electrically connected to at least microprocessor 106, and power generation circuit 108, which is in turn electrically connected to high voltage generation circuit 102. Olson, et al. U.S. Pat. No. 5,645,571 further describes and illustrates an AED electrical system like system 100.

A method of generating and applying defibrillation shock pulses of the present invention includes the following principles and steps. The most recent AAMI specification provides for a greater range of applying defibrillation shock pulses, particularly including a specification for applying a shock pulse to a 125 ohm impedance patient for which the maximum current is 20 amperes. In both the prior and most recent AAMI specifications, a maximum 20 ampere current was also specified for a 100 ohm patient. This relationship means that the voltage applied to the patient can be increased above 2,000 volts when the patient's impedance is above 100 ohms in order to achieve the maximum current of 20 amperes specified by the most recent AAMI specification for patient impedance up to 125 ohms.

Another significant principle changed in the most recent AAMI specification is that the voltage applied to the patient may be selected depending upon the transthoracic impedance of the patient. This principle is significant since the impedance of the patient is related to the voltage applied to the patient. In other words, the higher the impedance presented by the patient, the higher the initial voltage of the defibrillation shock pulse will be. The lower the impedance presented by the patient, the lower the initial voltage of the defibrillation shock pulse applied to the patient will be. Accordingly, applying an optimal voltage and current to the patient depends upon knowing the particular impedance of the patient, which can vary appreciably from patient to patient, and which varies depending upon the level of voltage applied to the patient. Accordingly, establishing an accurate and appropriate impedance level for a relatively high voltage which will be applied in a defibrillation shock pulse is necessary for achieving optimal defibrillation of a patient. With these principles and relationships in mind, the method of the present invention will be further presented according to these inventive insights.

FIG. 3 briefly illustrates the major steps of this method. First, an initial predetermined amount of energy/voltage is discharged to the patient as a shock pulse. Following the shock pulse, the recorded shock data is monitored for a patient-dependent electrical parameter. Second, a patient transthoracic impedance is determined based on the monitored patient-dependent electrical parameter. Third, a subsequent predetermined amount of energy/voltage, which is based on the patient impedance, is discharged to the patient as a shock pulse while further monitoring the patient-dependent electrical parameter. These major steps of the method of the present invention are presented in further detail in the following discussion.

In order to accurately determine the impedance of a patient that occurs during a defibrillation shock, patient impedance must be measured while high voltage is being delivered to the patient. Accordingly, in the method of the present invention, the first shock of an initial predetermined amount of energy/voltage is delivered without previously determining the patient impedance. For example, for the first shock, the AED device is preferably charged to 1900 volts and a 200 Joule shock is delivered to the patient.

After the first defibrillation shock is delivered to the patient, the impedance of the patient is calculated from physical measurements. The impedance may be calculated by using a patient-dependent electrical parameter such as current or discharge duration monitored during the defibrillation shock pulse. In a first example, the patient transthoracic impedance during a high voltage defibrillation shock is calculated by monitoring current during the defibrillation shock since the defibrillation voltage is known. A specific patient transthoracic impedance will yield a monitorable current by ohms law (V/I=R). A second means of measuring the impedance of the patient is to monitor the duration of the defibrillation shock pulse. Since the defibrillation voltage is known and the defibrillation shock is terminated after a duration that is sufficient to achieve the desired energy delivered (e.g. 200 Joules, 300 Joules, 360 Joules . . . ), the duration is a function of the impedance of the patient $(V_f=V_i e^{-t/RC})$ where $V_i$ is the initial shock pulse voltage and $V_f$ is the final shock pulse voltage. Accordingly, the patient impedance can be calculated from this equation.

Figure 4:
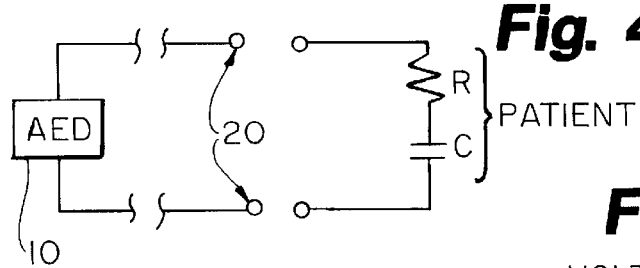
FIG. 4 is a schematic diagram of a quantitative patient model used in a method of the present invention.

The equation for calculating discharge duration is based on a well-known quantitative patient model shown in FIG. 4, in which electrodes 20 of AED 10 are connected to a patient. In this model, R represents patient transthoracic impedance and C represents a charge storage component of the patient. As may be appreciated by those skilled in the art, more sophisticated models can be used to represent patient transthoracic impedance.

After determining the impedance of the patient, the appropriate charge voltage is calculated for the next shock based on the calculated impedance and based on a patient-dependent electrical parameter using either of the above-identified methods. The charge voltage for the maximum allowed defibrillation current for the patient's impedance is then determined using the AAMI allowed current, the calculated patient impedance, and Ohms law.

Next, this calculated charge voltage and the maximum allowed current is applied to the patient through the electrodes 20 of AED 10 (FIG. 1). A desired patient-dependent electrical parameter (e.g. discharge duration or current) is monitored during the application of the charge voltage to the patient.

In accordance with traditional external defibrillation protocols, applying successively greater amounts of energy to the patient in repeated defibrillation shocks, subsequent defibrillation shocks are determined by using the monitored patient-dependent electrical parameter from the most recent defibrillation shock on the patient to calculate a patient impedance. The charge voltage necessary to deliver the maximum allowed defibrillation current to the patient's most recent impedance is determined using the AAMI allowed current, the calculated patient impedance, and Ohms law. Accordingly, as many subsequent defibrillation shocks as necessary are delivered to the patient wherein the charge voltage delivered in each of those subsequent shocks depends on a patient impedance calculated from a patient-dependent electrical parameter that was monitored during the most recent previous defibrillation shock.

Using this technique, each defibrillation shock is optimized to deliver the maximum allowed current by varying the charge voltage as necessary in light of the patient's transthoracic impedance presented during the defibrillation shock.

In staying with the AAMI specification, this approach yields a method of applying defibrillation waveforms in which a constant voltage of 2000 volts is applied for patient impedances up to 100 ohms with the maximum allowed current varying according to the AAMI specification, and in which a constant current waveform is used for patients over 100 ohms since the maximum allowed current in the most recent AAMI specification is 20 amperes at 125 ohms.

Moreover, using this approach results in a non-stepped approach to applying current to the patient. For example, under the most recent AAMI standard, the maximum allowed current ($I_{max}$) is 80 amps for a patient transthoracic impedance ($R_{patient}$) of 25 ohms. Similarly, $I_{max}$ is 40 amps for an $R_{patient}$ of 50 ohms, $I_{max}$ is 20 amps for an $R_{patient}$ of 100 ohms, and $I_{max}$ is 20 amps for an $R_{patient}$ of 125 ohms. A traditional stepped approach would apply 80 amps for all patient impedances between 25 and 50 ohms and apply 40 amps for all patient impedances between 50 and 100 ohms. Using the method of the present invention, the current applied to the patient for impedances between 25 and 50 ohms would vary between 80 amps and 40 amps, respectively, and would be determined by the specific impedance of the patient. For example, in the method of the present invention, if the actual patient impedance is 35 ohms, then for a 2000 volt applied voltage, the applied current would be 57 amps, according to Ohms law. This current would fall within the guidelines set by the AAMI standard yet tailor a defibrillation shock pulse to the specific transthoracic patient impedance instead of artificially applying a stepped current waveform for varying patient impedances.

Accordingly, with this approach, AED 10 (FIG. 1) and its electrical system 100 (FIG. 2) are programmed in advance with a waveform so that once a patient transthoracic impedance is determined, an appropriate current level is applied for a given voltage (2000 volts for impedances 100 ohms and below). Of course, as described above, a constant current of 20 amps is applied for patient impedances above 100 ohms. Accordingly, the AED 10 and its electrical system 100 are programmed to deliver optimal voltages which vary between 2000 volts and 2500 volts for patient impedances ranging between 100 ohms and 125 ohms, respectively. For example, using the method of the present invention, for a 115 ohm patient impedance based on a monitored patient-dependent electrical parameter, a 2300 volt charge would be identified from the programmed AED as being the appropriate voltage to apply to achieve the AAMI maximum allowed current of 20 amperes.

In accordance with the AAMI specification and the method of generating defibrillation waveforms of the present invention, resulting waveforms for varying patient impedances are depicted in the FIGS. 5–8. In these figures, voltage is represented on the Y axis of the voltage curve and is represented by the following equation:

$$V_f = V_i e^{\frac{-t}{R \cdot C}}. \tag{1}$$

The current curve is represented by the following equation:

$$I = \frac{V}{R}. \tag{2}$$

Figure 5A:
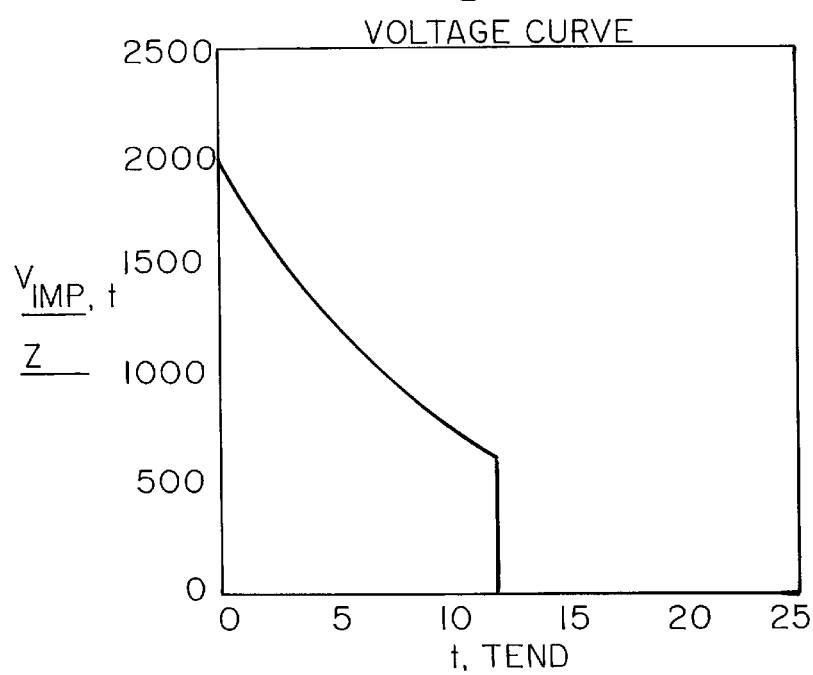
FIG. 5 is a schematic drawing of a defibrillation shock pulse waveform of the present invention for a patient having an impedance of 50 ohms.
Figure 5B:
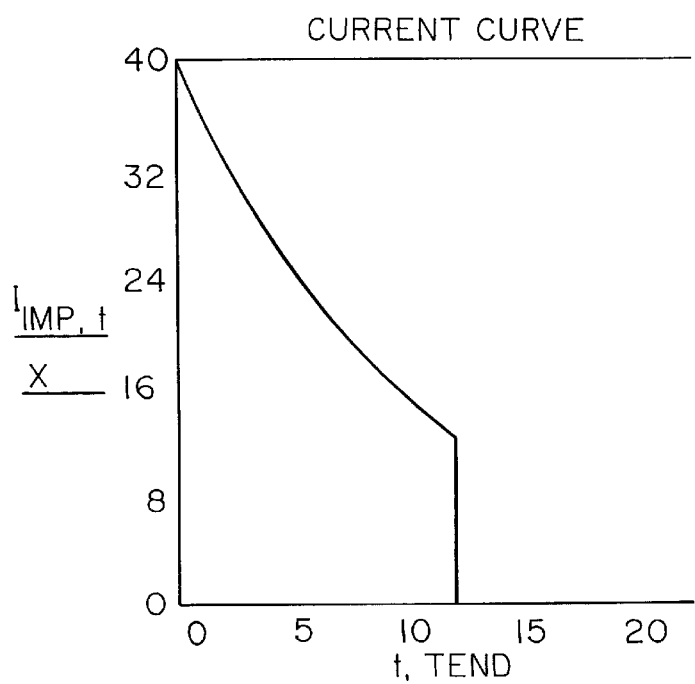
Figure 6A:
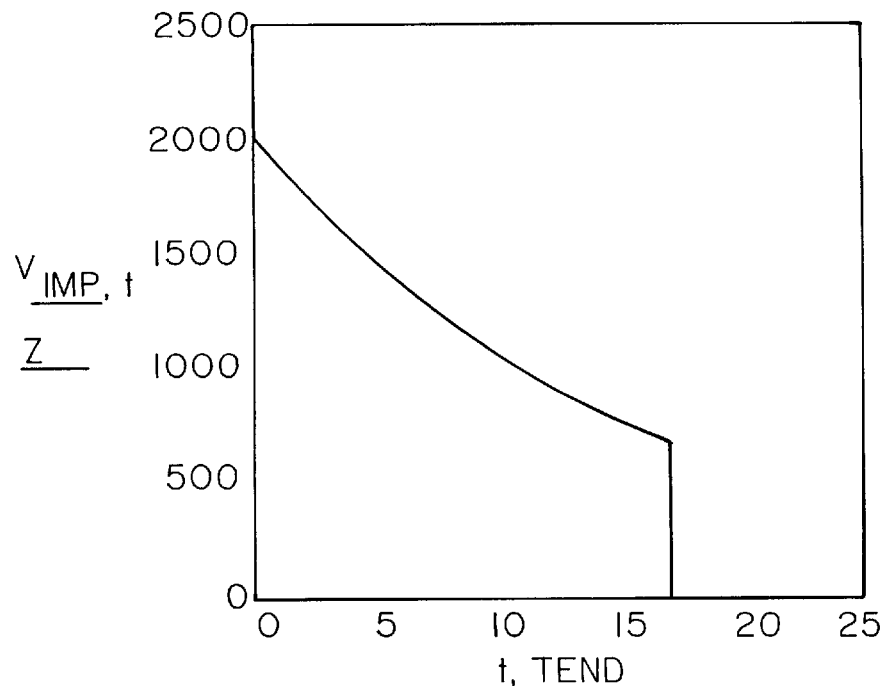
FIG. 6 is a schematic drawing of a defibrillation shock pulse waveform of the present invention for a patient having an impedance of 75 ohms.
Figure 6B:
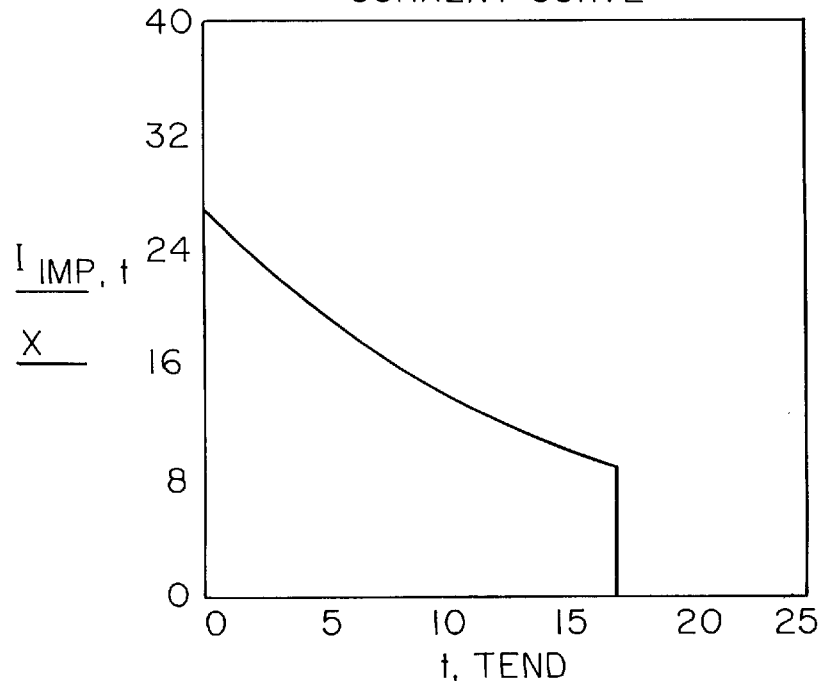
Figure 7A:
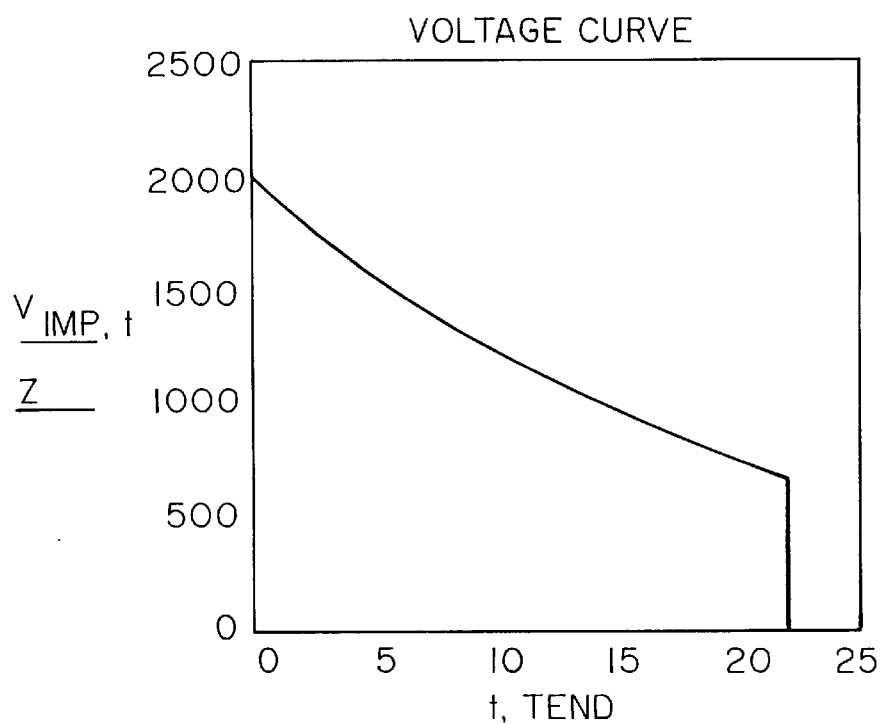
FIG. 7 is a schematic drawing of a defibrillation shock pulse waveform of the present invention for a patient having an impedance of 100 ohms.
Figure 7B:
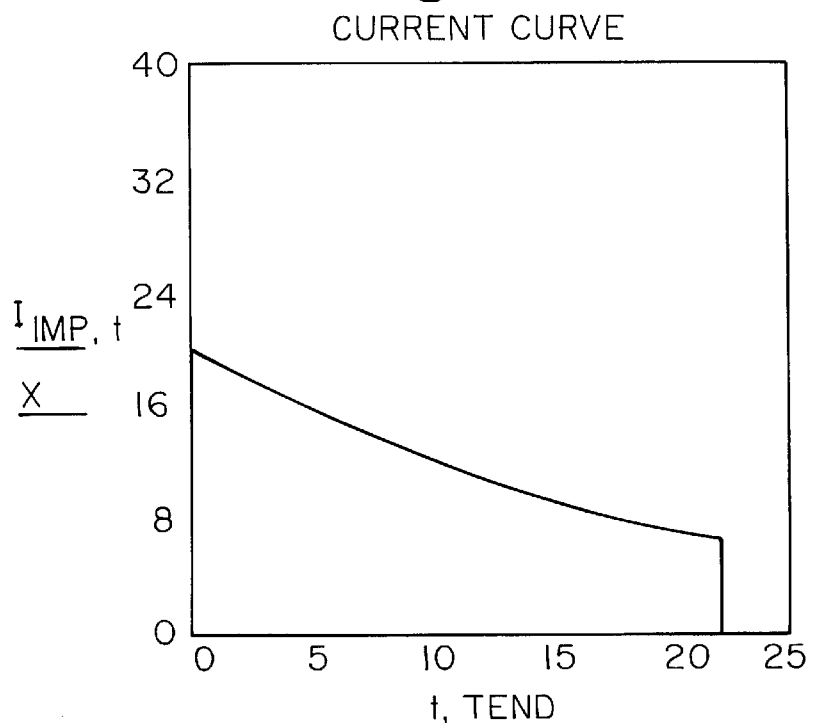
Figure 8A:
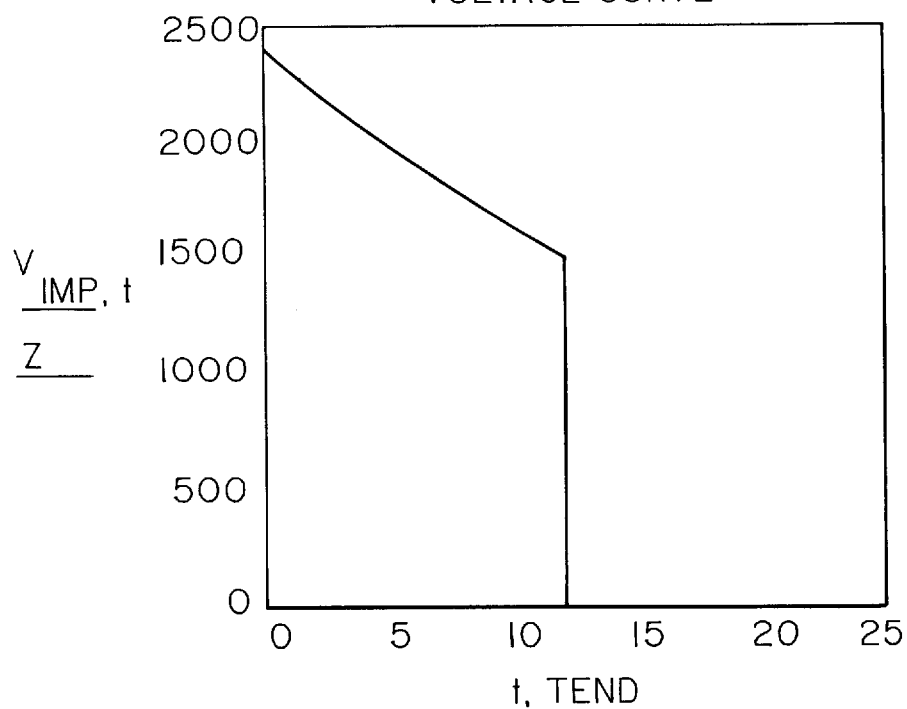
FIG. 8 is a schematic drawing of a defibrillation shock pulse waveform of the present invention for a patient having an impedance of 125 ohms.
Figure 8B:
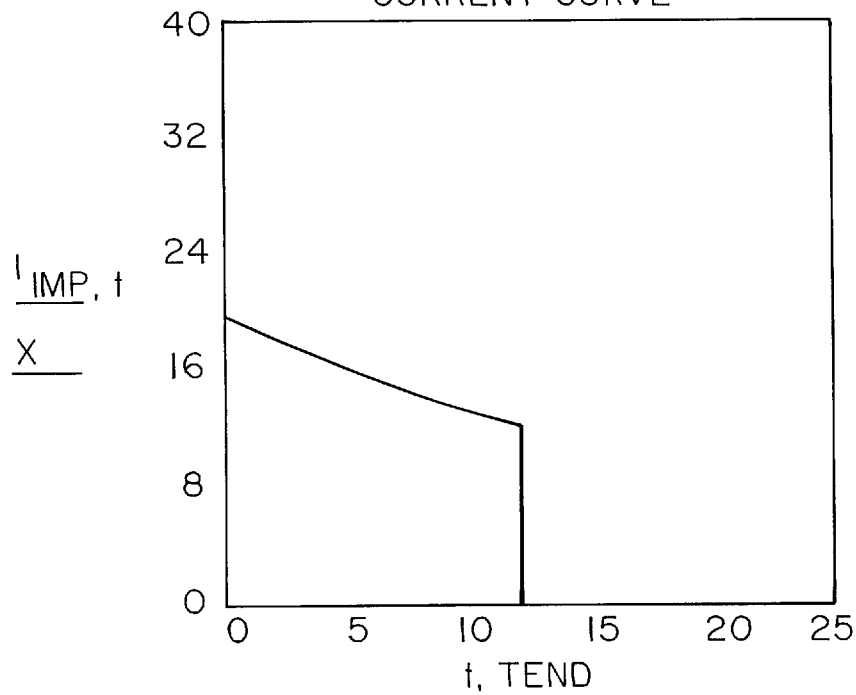

The voltage and current curve as shown in FIG. 5 is representative for a patient impedance of 50 ohms. The voltage and current curves in the subsequent FIGS. 6–8 are similarly represented by equations (1 and 2) for voltage and current, respectively. FIG. 6 provides voltage and current curves representative for a patient transthoracic impedance of 75 ohms, whereas FIGS. 7 and 8 provide voltage and current curves representative for patient impedances of 100 and 125 ohms respectively. While FIG. 8 illustrates the charge voltage being equal to 2400 volts for a patient transthoracic impedance of 125 ohms, a charge voltage of 2500 volts could be applied in the method of the present invention and still be within the maximum allowed current of 20 amps for a 125-volt patient under the AAMI specification.

Accordingly, the method of the present invention for generating defibrillator waveforms produces defibrillation shock pulses incorporating two key components. First, the voltage and energy applied to the patient is closely and accurately associated with a patient transthoracic impedance determined from a high-voltage defibrillation shock rather than from an artificially assumed patient impedance or from a low patient impedance measured during a low-voltage defibrillation shock. Second, the method of the present invention applies chargeable voltages based upon specific patient impedances to maximize AAMI allowed current throughout a continuum of patient transthoracic impedances rather than artificially applying a stepped amount of current/voltage based only on milestone patient impedances (e.g. 25 ohms, 50 ohms, 100 ohms and 125 ohms). All of these factors, which are combined into a method of generating a defibrillation waveform of the present invention, result in a defibrillation shock pulse being applied from an AED that is specifically tailored to each patient and specifically tailored as necessary from shock to shock.

Although the present invention has been described with reference to preferred embodiments, workers skilled in the art will recognize the changes may be made in form and detail without departing from the spirit and scope of the invention.

What is claimed is:

1. A method for applying a defibrillation shock pulse to a patient through electrodes connected to a defibrillator, the method comprising the steps of:

(a) applying an initial defibrillation pulse of a predetermined amount of energy without previously determining a transthoracic impedance from a defibrillator to a patient while monitoring an initial patient-dependent electrical parameter;

(b) determining a transthoracic impedance of the patient based on the monitored patient-dependent electrical parameter;

(c) applying a subsequent calculated amount of energy from the defibrillator to the patient based on the determined transthoracic patient impedance while monitoring a subsequent patient-dependent electrical parameter;

(d) repeating steps (b)–(c) a plurality of times wherein the impedance determined in step (b) is based on the subsequent patient-dependent electrical parameter monitored in step (c).

2. The method of claim 1 wherein step (a) is performed without previously monitoring a patient-dependent electrical parameter for determining at least one of a voltage, duration, and current of the defibrillation shock pulse.

3. The method of claim 1 wherein the patient-dependent electrical parameter is current.

4. The method of claim 1 wherein the patient-dependent electrical parameter is a discharge duration.

5. The method of claim 4 wherein the discharge duration is calculated from the equation $V=Ve^{(-t/RC)}$, where, t is the duration, V is the voltage applied to the patient to delivery the amount of energy, and RC is the time constant of a quantitative defibrillation model of a chest of the patient, wherein R represents the patient transthoracic impedance and C represents a capacitive component of the defibrillator.

6. The method of claim 1 wherein the initial predetermined amount of energy and the subsequent calculated amount of energy further comprise a charge voltage.

7. The method of claim 1 wherein the initial predetermined amount of energy further comprises an initial predetermined amount of voltage and the subsequent calculated amount of energy further comprises a subsequent calculated amount of voltage wherein the initial predetermined amount of voltage is less than the subsequent calculated amount of voltage.

8. The method of claim 1 wherein the shock pulse is applied in a monophasic truncated exponential waveform.

9. The method of claim 1 wherein the shock pulse is applied in a biphasic truncated exponential waveform.

10. A method for applying electrotherapy to a patient through electrodes adapted to be connected externally to said patient, the electrodes being connected to an energy source, the method comprising the steps of:

(a) charging an energy source to a first predetermined defibrillation pulse level;

(b) discharging a first application of the energy source across electrodes to deliver the first predetermined defibrillation pulse amount of energy to a patient without previously determining a transthoracic impedance;

(c) monitoring a patient-dependent electrical parameter during the first discharging step;

(d) determining a first transthoracic impedance based on the monitored patient-dependent electrical parameter;

(e) charging the energy source to a second calculated level based on the determined patient transthoracic impedance and on a predetermined current and impedance relationship; and (f) discharging a second application of the energy source across the electrodes to deliver the second calculated amount of energy to the patient.

11. The method of claim 10 wherein the first predetermined defibrillation pulse level in the charging step further comprises a predetermined amount of voltage.

12. The method of claim 11 wherein the voltage is about 1900 Volts and the predetermined defibrillation pulse amount of energy in the discharging step is about 200 Joules.

13. The method of claim 10 wherein in the charging step, the first predetermined defibrillation pulse level of energy includes a first predetermined voltage.

14. The method of claim 10 wherein the patient dependent electrical parameter is current.

15. The method of claim 14 wherein the current is direct current.

16. The method of claim 10 wherein the patient dependent electrical parameter is a duration of the discharging step (b).

17. The method of claim 16 wherein in the charging step, the first predetermined defibrillation pulse level includes a first predetermined charge voltage.

18. The method of claim 17 wherein the duration is calculated from the equation $V=Ve^{(-t/RC)}$, where, t is the discharge duration, V is the voltage applied to the patient to deliver the amount of energy, and RC is the time constant of a quantitative defibrillation model of a chest of the patient, wherein R represents the patient transthoracic impedance and C represents a capacitive component of the defibrillator.

19. The method of claim 10 wherein the first predetermined amount of energy is less than the second calculated amount of energy.

20. The method of claim 19 wherein a third calculated amount of energy is greater than the second calculated amount of energy.

21. The method of claim 10 and further comprising:

(g) monitoring the patient-dependent electrical parameter during the second discharging step (f);

(h) determining a second patient transthoracic impedance based on the monitored electrical parameter;

(i) charging the energy source to a third calculated level of energy based on the second determined patient impedance and on a predetermined current and impedance relationship; and (j) discharging a third application of the energy source across the electrodes to deliver a third calculated amount of energy to the patient.

22. The method of claim 10 wherein the electrotherapy is applied in a monophasic truncated exponential waveform.

23. The method of claim 10 wherein the electrotherapy is applied in a biphasic truncated exponential waveform.

24. The method of claim 10 wherein the waveform is a continuous monophasic truncated exponential waveform that delivers a predetermined amount of energy to the patient and is shaped according to the following criteria:

a maximum peak voltage and a duration of the waveform are based on a predetermined maximum peak current according to a cardiac defibrillation standard for a monitored patient transthoracic impedance.

25. The method of claim 24 wherein $I_{max}$ represents the predetermined maximum peak current and $R_{patient}$ represents the monitored patient impedance, and wherein the cardiac defibrillation standard comprises:

$I_{max}$ is 80 amps when $R_{patient}$ is 25 ohms,
$I_{max}$ is 40 amps when $R_{patient}$ is 50 ohms,
$I_{max}$ is 20 amps when $R_{patient}$ is 100 ohms, and
$I_{max}$ is 20 amps when $R_{patient}$ is 125 ohms.

26. The method of claim 10 wherein the waveform is a continuous biphasic truncated exponential waveform that delivers a predetermined amount of energy to the patient and is shaped according to the following criteria:

a maximum peak voltage and a duration of a first phase of the biphasic waveform are based on a predetermined maximum peak current according to a cardiac defibrillation standard for a monitored patient transthoracic impedance.

27. A method for applying a defibrillation shock pulse to a patient through electrodes connected to a defibrillator, the method comprising the steps of:

(a) applying an initial predetermined defibrillation pulse without previously determining a transthoracic impedance to the patient while monitoring a patient-dependent electrical parameter; and (b) iteratively applying a subsequent calculated amount of voltage to the patient based on a patient transthoracic impedance determined from the patient-dependent electrical parameter monitored in a prior application of voltage to the patient.

28. The method of claim 27 wherein the voltage in step (a) is on the order of 1900 volts.

29. The method of claim 27 wherein the voltage in step (b) is a single preselected voltage applied to the patient when the patient impedance is no greater than 100 ohms, and a single preselected current applied to the patient when the patient impedance is greater than 100 ohms.

30. The method of claim 29 wherein for patient impedances between 25 ohms and 50 ohms, the applied current is between 80 ohms and 40 ohms, and for patient impedances between 50 ohms and 100 ohms, the applied current is between 40 amps and 20 amps, and wherein the applied current is determined according to Ohms law with the applied charge voltage being 2000 volts.

31. The method of claim 29 wherein for patient impedances between 100 ohms and 125 ohms, the applied voltage is between 2000 volts and 2500 volts, and is determined according to Ohms law with the applied current being 20 amps.

* * * * *